United States Patent [19]
Heyneker et al.

[11] Patent Number: 5,756,093
[45] Date of Patent: May 26, 1998

[54] TISSUE PLASMINOGEN ACTIVATOR VARIANTS

[75] Inventors: Herbert L. Heyneker, Hillsborough; Gordon A. Vehar, San Carlos; Nicholas F. Paoni, Moraga; William F. Bennett, San Mateo, all of Calif.

[73] Assignee: Genentech, Inc., So. San Francisco, Calif.

[21] Appl. No.: 275,335

[22] Filed: Jul. 14, 1994

Related U.S. Application Data

[63] Continuation of Ser. No. 126,114, Sep. 23, 1993, abandoned, which is a continuation of Ser. No. 808,537, Dec. 16, 1991, abandoned, which is a continuation-in-part of Ser. No. 741,120, Aug. 5, 1991, Pat. No. 5,147,643, which is a division of Ser. No. 522,480, May 11, 1990, Pat. No. 5,073,494, which is a continuation of Ser. No. 186,494, Apr. 26, 1988, abandoned, which is a continuation of Ser. No. 71,506, Jul. 9, 1987, abandoned, which is a continuation of Ser. No. 846,697, Apr. 1, 1986, abandoned, which is a continuation of Ser. No. 725,468, Apr. 22, 1985, abandoned.

[51] Int. Cl.[6] ................ A61K 38/48; C12N 9/48; C12N 1/21; C07H 21/04
[52] U.S. Cl. ............ 424/94.64; 435/212; 435/320.1; 435/325; 435/252.3; 536/23.2
[58] Field of Search ................ 424/94.63, 94.64; 435/172.3, 212, 226, 320.1, 240.2, 252.3; 536/23.2

[56] References Cited

U.S. PATENT DOCUMENTS

| | | | |
|---|---|---|---|
| 4,753,879 | 6/1988 | Rosa | 435/172.3 |
| 4,766,075 | 8/1988 | Goeddel et al. | 435/240.2 |
| 4,889,722 | 12/1989 | Sheffield et al. | 424/450 |
| 5,108,901 | 4/1992 | Anderson et al. | 435/23 |

FOREIGN PATENT DOCUMENTS

| | | |
|---|---|---|
| 93619 | 11/1983 | European Pat. Off. |
| 199574 | 10/1986 | European Pat. Off. |
| 201153 | 11/1986 | European Pat. Off. |
| 233013 | 8/1987 | European Pat. Off. |
| 241209 | 10/1987 | European Pat. Off. |
| 292009 | 11/1988 | European Pat. Off. |
| 293934 | 12/1988 | European Pat. Off. |
| 293936 | 12/1988 | European Pat. Off. |
| 8810119 | 12/1988 | WIPO . |

OTHER PUBLICATIONS

Bennett et al. Jour. Biol. Chem. 266 , 5191 (1991).
Pennica, D. et al., Nature, vol. 301, pp. 214–221, 1983.
Tate, K. et al., Biochemistry, vol. 26, pp. 338–343, Jan. 1987.

*Primary Examiner*—Robert A. Wax
*Assistant Examiner*—Kowai Lau
*Attorney, Agent, or Firm*—Walter H. Dreger

[57] ABSTRACT

Biologically active variant tissue plasminogen activators are disclosed. The disclosure focuses on position 276 variants that exhibit enhanced fibrin specificity.

18 Claims, 5 Drawing Sheets

```
GTTCTGAGCA CAGGGCTGGA GAGAAAACCT CTGCGAGGAA AGGGAAGGAG CAAGCCGTGA    60

ATTTAAGGGA CGCTGTGAAG CAATC ATG GAT GCA ATG AAG AGA GGG CTC TGC    112
                            Met Asp Ala Met Lys Arg Gly Leu Cys
                            -35              -30

TGT GTG CTG CTG CTG TGT GGA GCA GTC TTC GTT TCG CCC AGC CAG GAA    160
Cys Val Leu Leu Leu Cys Gly Ala Val Phe Val Ser Pro Ser Gln Glu
    -25             -20                 -15

ATC CAT GCC CGA TTC AGA AGA GGA GCC AGA TCT TAC CAA GTG ATC TGC    208
Ile His Ala Arg Phe Arg Arg Gly Ala Arg Ser Tyr Gln Val Ile Cys
-10             -5                   1               5

AGA GAT GAA AAA ACG CAG ATG ATA TAC CAG CAA CAT CAG TCA TGG CTG    256
Arg Asp Glu Lys Thr Gln Met Ile Tyr Gln Gln His Gln Ser Trp Leu
                10              15              20

CGC CCT GTG CTC AGA AGC AAC CGG GTG GAA TAT TGC TGG TGC AAC AGT    304
Arg Pro Val Leu Arg Ser Asn Arg Val Glu Tyr Cys Trp Cys Asn Ser
        25              30              35

GGC AGG GCA CAG TGC CAC TCA GTG CCT GTC AAA AGT TGC AGC GAG CCA    352
Gly Arg Ala Gln Cys His Ser Val Pro Val Lys Ser Cys Ser Glu Pro
    40              45              50

AGG TGT TTC AAC GGG GGC ACC TGC CAG CAG GCC CTG TAC TTC TCA GAT    400
Arg Cys Phe Asn Gly Gly Thr Cys Gln Gln Ala Leu Tyr Phe Ser Asp
55              60              65              70

TTC GTG TGC CAG TGC CCC GAA GGA TTT GCT GGG AAG TGC TGT GAA ATA    448
Phe Val Cys Gln Cys Pro Glu Gly Phe Ala Gly Lys Cys Cys Glu Ile
                75              80              85

GAT ACC AGG GCC ACG TGC TAC GAG GAC CAG GGC ATC AGC TAC AGG GGC    496
Asp Thr Arg Ala Thr Cys Tyr Glu Asp Gln Gly Ile Ser Tyr Arg Gly
            90              95              100

ACG TGG AGC ACA GCG GAG AGT GGC GCC GAG TGC ACC AAC TGG AAC AGC    544
Thr Trp Ser Thr Ala Glu Ser Gly Ala Glu Cys Thr Asn Trp Asn Ser
    105             110             115

AGC GCG TTG GCC CAG AAG CCC TAC AGC GGG CGG AGG CCA GAC GCC ATC    592
Ser Ala Leu Ala Gln Lys Pro Tyr Ser Gly Arg Arg Pro Asp Ala Ile
120             125             130

AGG CTG GGC CTG GGG AAC CAC AAC TAC TGC AGA AAC CCA GAT CGA GAC    640
Arg Leu Gly Leu Gly Asn His Asn Tyr Cys Arg Asn Pro Asp Arg Asp
135             140             145             150

TCA AAG CCC TGG TGC TAC GTC TTT AAG GCG GGG AAG TAC AGC TCA GAG    688
Ser Lys Pro Trp Cys Tyr Val Phe Lys Ala Gly Lys Tyr Ser Ser Glu
            155             160             165

TTC TGC AGC ACC CCT GCC TGC TCT GAG GGA AAC AGT GAC TGC TAC TTT    736
Phe Cys Ser Thr Pro Ala Cys Ser Glu Gly Asn Ser Asp Cys Tyr Phe
        170             175             180
```

FIG._2A

```
GGG AAT GGG TCA GCC TAC CGT GGC ACG CAC AGC CTC ACC GAG TCG GGT    784
Gly Asn Gly Ser Ala Tyr Arg Gly Thr His Ser Leu Thr Glu Ser Gly
        185             190             195

GCC TCC TGC CTC CCG TGG AAT TCC ATG ATC CTG ATA GGC AAG GTT TAC    832
Ala Ser Cys Leu Pro Trp Asn Ser Met Ile Leu Ile Gly Lys Val Tyr
        200             205             210

ACA GCA CAG AAC CCC AGT GCC CAG GCA CTG GGC CTG GGC AAA CAT AAT    880
Thr Ala Gln Asn Pro Ser Ala Gln Ala Leu Gly Leu Gly Lys His Asn
215             220             225             230

TAC TGC CGG AAT CCT GAT GGG GAT GCC AAG CCC TGG TGC CAC GTG CTG    928
Tyr Cys Arg Asn Pro Asp Gly Asp Ala Lys Pro Trp Cys His Val Leu
            235             240             245

AAG AAC CGC AGG CTG ACG TGG GAG TAC TGT GAT GTG CCC TCC TGC TCC    976
Lys Asn Arg Arg Leu Thr Trp Glu Tyr Cys Asp Val Pro Ser Cys Ser
        250             255             260

ACC TGC GGC CTG AGA CAG TAC AGC CAG CCT CAG TTT CGC ATC AAA GGA   1024
Thr Cys Gly Leu Arg Gln Tyr Ser Gln Pro Gln Phe Arg Ile Lys Gly
        265             270             275

GGG CTC TTC GCC GAC ATC GCC TCC CAC CCC TGG CAG GCT GCC ATC TTT   1072
Gly Leu Phe Ala Asp Ile Ala Ser His Pro Trp Gln Ala Ala Ile Phe
        280             285             290

GCC AAG CAC AGG AGG TCG CCC GGA GAG CGG TTC CTG TGC GGG GGC ATA   1120
Ala Lys His Arg Arg Ser Pro Gly Glu Arg Phe Leu Cys Gly Gly Ile
295             300             305             310

CTC ATC AGC TCC TGC TGG ATT CTC TCT GCC GCC CAC TGC TTC CAG GAG   1168
Leu Ile Ser Ser Cys Trp Ile Leu Ser Ala Ala His Cys Phe Gln Glu
            315             320             325

AGG TTT CCG CCC CAC CAC CTG ACG GTG ATC TTG GGC AGA ACA TAC CGG   1216
Arg Phe Pro Pro His His Leu Thr Val Ile Leu Gly Arg Thr Tyr Arg
        330             335             340

GTG GTC CCT GGC GAG GAG GAG CAG AAA TTT GAA GTC GAA AAA TAC ATT   1264
Val Val Pro Gly Glu Glu Glu Gln Lys Phe Glu Val Glu Lys Tyr Ile
        345             350             355

GTC CAT AAG GAA TTC GAT GAT GAC ACT TAC GAC AAT GAC ATT GCG CTG   1312
Val His Lys Glu Phe Asp Asp Asp Thr Tyr Asp Asn Asp Ile Ala Leu
        360             365             370

CTG CAG CTG AAA TCG GAT TCG TCC CGC TGT GCC CAG GAG AGC AGC GTG   1360
Leu Gln Leu Lys Ser Asp Ser Ser Arg Cys Ala Gln Glu Ser Ser Val
375             380             385             390

GTC CGC ACT GTG TGC CTT CCC CCG GCG GAC CTG CAG CTG CCG GAC TGG   1408
Val Arg Thr Val Cys Leu Pro Pro Ala Asp Leu Gln Leu Pro Asp Trp
            395             400             405
```

FIG._2B

```
ACG GAG TGT GAG CTC TCC GGC TAC GGC AAG CAT GAG GCC TTG TCT CCT   1456
Thr Glu Cys Glu Leu Ser Gly Tyr Gly Lys His Glu Ala Leu Ser Pro
            410                     415                 420

TTC TAT TCG GAG CGG CTG AAG GAG GCT CAT GTC AGA CTG TAC CCA TCC   1504
Phe Tyr Ser Glu Arg Leu Lys Glu Ala His Val Arg Leu Tyr Pro Ser
            425                     430                 435

AGC CGC TGC ACA TCA CAA CAT TTA CTT AAC AGA ACA GTC ACC GAC AAC   1552
Ser Arg Cys Thr Ser Gln His Leu Leu Asn Arg Thr Val Thr Asp Asn
            440                     445                 450

ATG CTG TGT GCT GGA GAC ACT CGG AGC GGC GGG CCC CAG GCA AAC TTG   1600
Met Leu Cys Ala Gly Asp Thr Arg Ser Gly Gly Pro Gln Ala Asn Leu
455                     460                     465             470

CAC GAC GCC TGC CAG GGC GAT TCG GGA GGC CCC CTG GTG TGT CTG AAC   1648
His Asp Ala Cys Gln Gly Asp Ser Gly Gly Pro Leu Val Cys Leu Asn
                475                     480                 485

GAT GGC CGC ATG ACT TTG GTG GGC ATC ATC AGC TGG GGC CTG GGC TGT   1696
Asp Gly Arg Met Thr Leu Val Gly Ile Ile Ser Trp Gly Leu Gly Cys
            490                     495                 500

GGA CAG AAG GAT GTC CCG GGT GTG TAC ACC AAG GTT ACC AAC TAC CTA   1744
Gly Gln Lys Asp Val Pro Gly Val Tyr Thr Lys Val Thr Asn Tyr Leu
            505                     510                 515

GAC TGG ATT CGT GAC AAC ATG CGA CCG TGACCAGGA ACACCCGACT           1790
Asp Trp Ile Arg Asp Asn Met Arg Pro Op
            520                 525

CCTCAAAAGC AAATGAGATC CCGCCTCTTC TTCTTCAGAA GACACTGCAA AGGCGCAGTG 1850
CTTCTCTACA GACTTCTCCA GACCCACCAC ACCGCAGAAG CGGGACGAGA CCCTACAGGA 1910
GAGGGAAGAG TGCATTTTCC CAGATACTTC CCATTTTGGA AGTTTTCAGG ACTTGGTCTG 1970
ATTTCAGGAT ACTCTGTCAG ATGGGAAGAC ATGAATGCAC ACTAGCCTCT CCAGGAATGC 2030
CTCCTCCCTG GCAGAAAGT GGCCATGCCA CCCTGTTTTC AGCTAAAGCC CAACCTCCTG 2090
ACCTGTCACC GTGAGCAGCT TTGGAAACAG GACCACAAAA ATGAAAGCAT GTCTCAATAG 2150
TAAAAGATAA CAAGATCTTT CAGGAAAGAC GGATTGCATT AGAAATAGAC AGTATATTTA 2210
TAGTCACAAG AGCCCAGCAG GGCCTCAAAG TTGGGGCAGG CTGGCTGGCC CGTCATGTTC 2270
CTCAAAAGCA CCCTTGACGT CAAGTCTCCT TCCCCTTTCC CCACTCCCTG GCTCTCAGAA 2330
GGTATTCCTT TTGTGTACAG TGTGTAAAGT GTAAATCCTT TTTCTTTATA AACTTTAGAG 2390
TAGCATGAGA GAATTGTATC ATTTGAACAA CTAGGCTTCA GCATATTTAT AGCAATCCAT 2450
GTTAGTTTTT ACTTTCTGTT GCCACAACCC TGTTTTATAC TGTACTTAAT AAATTCAGAT 2510
ATATTTTTCA CAGTTTTTCC AAAAAAAAAA AAAA                              2544
```

TISSUE PLASMINOGEN ACTIVATOR VARIANTS

This is a continuation of application Ser. No. 08/126,114 filed 23 Sep. 1993, now abandoned, which is a continuation of application Ser. No. 07/808,537 filed 16 Dec. 1991, now abandoned, which is a continuation-in-part of application Ser. No. 07/741,120 filed 5 Aug. 1991, now U.S. Pat. No. 5,147,643, which is a division of application Ser. No. 07/522,480 filed 11 May 1990, now U.S Pat. No. 5,073,494, which is a continuation of application Ser. No. 07/186,494 filed 26 Apr. 1988, abandoned, which is a continuation of application Ser. No. 07/071,506 filed 9 Jul. 1987, abandoned, which is a continuation of application Ser. No. 06/846,697 filed 1 Apr. 1986, abandoned, which is a continuation of application Ser. No. 06/725,468 filed 22 Apr. 1985, abandoned.

This application is related to application Ser. No. 07/808,366 filed on even date therewith.

FIELD OF THE INVENTION

The present invention is directed to particular novel variants of tissue plasminogen activator (t-PA). These variants, although embraced generically by earlier disclosure, as noted infra, are novel, specific derivatives which exhibit activities which defied prediction from the prior research of others on the basic tissue plasminogen activator molecule or the model serine proteases trypsin and chymotrypsin.

As the preferred embodiment herein contemplates the preparation of such variants via recombinant DNA technology, the present invention likewise encompasses the associated compounds and means involved in such technology, namely, DNA isolates encoding such variants, expression vectors, transfected host cells and processes for making and using each of them. The novel variants hereof have unexpectedly enhanced fibrin specificity.

BACKGROUND OF THE INVENTION

Plasminogen activators are enzymes that activate the zymogen plasminogen to generate the serine proteinase plasmin (by cleavage at Arg561-Val562) that degrades various proteins, including fibrin. Among the plasminogen activators studied are streptokinase, a bacterial protein, urokinase, an enzyme synthesized in the kidney and elsewhere and originally extracted from urine, and tissue plasminogen activator (t-PA), an enzyme produced by the cells lining blood vessel walls.

The mechanism of action of each of these plasminogen activators differs: Streptokinase forms a complex with plasminogen or plasmin, generating plasminogen-activating activity, urokinase cleaves plasminogen directly, and t-PA requires fibrin to yield maximum plasminogen activating activity.

t-PA has been identified and described as a particularly important and potent new biological pharmaceutical agent that has shown extraordinary results in the treatment of vascular diseases, such as myocardial infarction and pulmonary embolism, due in part to its fibrin specificity and potent ability to dissolve blood clots in vivo.

Tissue plasminogen activator was first identified as a substantially pure isolate from a natural source, and tested for requisite plasminogen activator activity by Collen, et al., European Patent Application Publication No. 041766, published 16 Dec. 1981, based upon a first filing of 11 Jun. 1980. See also U.S. Pat. No. 4,752,603, issued 21 Jun. 1988 and Rijken, et al., *J. Biol. Chem.* 256, 7035 (1981).

Subsequently, researchers in Assignee's laboratories produced large quantities of tissue plasminogen activator, fully characterized by underlying DNA and deduced amino acid sequences, essentially free of proteins with which it is ordinarily associated, in a distinct milieu, via recombinant DNA technology. This work has been recorded in the scientific literature and in European Patent Application Publication No. 093619 published 9 Nov. 1983, based upon a first filing on 5 May 1982. See also U.S. Pat. No. 4,766,075, issued 23 Aug. 1988 and Pennica, et al., *Nature* 301, 214 (1983). The above patent application (EPO Publication No. 093619) contemplates the production of various human plasminogen activator derivatives, variously modified by amino acid substitutions, deletions, additions, or replacements prepared, for example, by site directed mutagenesis of the underlying DNA.

Despite the profound advantages associated with natural t-PA as a clot-dissolving agent, it is not believed that the natural protein necessarily represents the optimal t-PA agent under all circumstances. Therefore, several variants have been proposed or devised to enhance specific properties of t-PA. Certain of those variants address disadvantages associated with the use of natural t-PA in situations where an agent with a longer half-life or slower clearance rate would be preferred, e.g., in the treatment of deep-vein thrombosis and following reperfusion of an infarct victim, or where a single-chain agent is preferred.

For further patent literature regarding modification of the protease cleavage site of t-PA, see, for example, EPO Pat. Nos. 241,209; EP 201,153 published Nov. 12, 1986; EP 233,013 published Aug. 19, 1987; EP 293,936 published Dec. 7, 1988; and EP 293,934 published Dec. 7, 1988; and WO 88/10119.

EP 292009, published 23 Nov. 1988 (priority 22 May 1987) refers to t-PA "homologs" including t-PAs having certain amino acid substitutions at positions 274–277. Other more radical homologs are described. A single 276 "homolog" has proline substituted for isoleucine.

It would also be desirable to provide a t-PA molecule that, relative to wild-type t-PA, has a higher ratio of fibrin-stimulated (or a plasma clot-stimulated) activity to fibrinogen-stimulated (or plasma-stimulated) activity, i.e., is more fibrin (or plasma clot) specific, so that it will act only at the site of the clot and not systemically. Accordingly, it is an object of this invention to provide fibrin-specific t-PA molecules that exhibit improved therapeutic and pharmaceutical characteristics.

It is another object to provide for the treatment of conditions that admit the use of clot-dissolving agents that are active only at the site of the clot and are useful at higher levels than other such agents.

SUMMARY OF THE INVENTION

The present application is directed to novel variants of t-PA, which exhibit surprisingly enhanced fibrin specificity. Particular specific variants hereof are those having an amino acid other than isoleucine at a position corresponding to position 276 of the amino acid sequence of wild-type t-PA. Certain of these variants have no other amino acid substitution within the 275–277 position range. By position 276 is meant the 276th amino acid from the N-terminus of the 527 total amino acid sequence of mature, wild-type t-PA molecule.

Certain of these 276 variants are resistant more or less to proteolytic cleavage at the known 275/276 cleavage site.

Thus, an embodiment exhibited herein with respect to imparting resistance to cleavage, and/or fibrin specificity, is to modify an amino acid between two particular 275/276 and 277/278 sites. A particular embodiment is to modify the amino acid between those two 275/276 and 277/278 sites, namely, amino acid 276 preparing, as examples, 276 t-PA variants, e.g., P276 t-PA, D276 t-PA, S276 t-PA, A276 t-PA, H276 t-PA, W276 t-PA, Y276 t-PA, etc. Other further 276 variants contemplated herein are E275P276 t-PA, P276I277 t-PA, and E275P276I277 t-PA, and further mutagenesis within the about 270 to about 279 region, or any other site, follows from the context of the present invention, one endpoint being measured by the susceptibility of cleavage(s) of the resultant t-PA molecule, and/or another endpoint being measured by increased fibrin specificity.

It has been determined herein that variants at the 276 position exhibit unexpectedly enhanced fibrin specificity compared with wild-type t-PA. Certain preferred such 276 variants have no further variance at any other position within the 275–277 range or within the 270–279 broader range.

Also included within the scope of this invention are the associated compounds and means for preparing the variants hereof using the preferred mode of recombinant DNA technology, namely, DNA isolates encoding such variants, expression vectors, transfected host cells and processes for making and using each of them.

In yet another embodiment, the invention is directed to a composition for treating a vascular condition or disease comprising a therapeutically effective amount of the variant herein in admixture with a pharmaceutically acceptable carrier.

Also encompassed herein is a composition for preventing fibrin deposition or adhesion formation or reformation comprising a therapeutically effective amount of the variant herein in admixture with a pharmaceutically acceptable carrier.

In still another embodiment, the invention provides a method of treating a vascular condition or disease in a mammal comprising administering an effective amount of the appropriate composition described above to the mammal.

An important aspect of this invention is to obtain a t-PA molecule that is more fibrin specific so that it will act more preferentially at the site of the clot than unmodified t-PA.

BRIEF DESCRIPTION OF THE DRAWINGS

FIGS. 2a, b and c represent the DNA and amino acid sequences of t-PA including 5' and 3'-untranslated regions.

DETAILED DESCRIPTION

As used herein, "tissue plasminogen activator", "human tissue plasminogen activator", "human t-PA", or "t-PA" denotes human extrinsic (tissue-type) plasminogen activator as produced, e.g., by recombinant cell culture systems, in bioactive forms comprising protease portion and corresponding to the plasminogen activator otherwise native to human tissue. It will be understood that natural allelic variations exist and occur from individual to individual, demonstrated by (an) amino acid difference(s) in the overall sequence. In addition, glycosylation patterns will depend on the nature of the host cellular environment.

Further, the terms contemplate "bioequivalent molecules" containing other amino acid differences in the overall sequence, beyond (naturally occurring) alleles. These may be purposefully introduced or result inadvertently such as via errors in cloning, etc.

As used herein, the term "wild-type t-PA" refers to the t-PA encoded by the CDNA reported by U.S. Pat. No. 4,766,075, supra, the disclosure of which is expressly incorporated herein by reference. The t-PA thus encoded is suitably a t-PA molecule from any native source or any recombinant expression system, including 293 or 294 cells, Chinese hamster ovary cells, etc.

It seems now clear that the human tissue plasminogen activator molecule contains five domains (stretches of amino acid sequence) that have been defined with reference to homologous or otherwise similar structures identified in various other proteins such as trypsin, chymotrypsin, plasminogen, prothrombin, fibronectin and epidermal growth factor. These domains have been designated, starting at the N-terminus of the amino acid sequence of human tissue plasminogen activator, as 1) the finger region (F) that has variously been defined as including amino acid 1 upwards of about 44, 2) the growth factor region (C) that has been variously defined as stretching from about amino acid 45 upwards of amino acid 91 (based upon its homology with EGF), 3) kringle one (K1) that has been defined as stretching from about amino acid 92 to about 173, 4) kringle two (K2) that has been defined as stretching from about amino acid 180 to about amino acid 261 and 5) the so-called serine protease domain (P) that generally has been defined as stretching from about amino acid 264 to the C-terminal end of the molecule. These domains are situated contiguously generally of one another, or are separated by short "linker" regions, and account for the entire amino acid sequence from about 1 to 527 amino acids in its putative mature form.

A "two-chain cleavage site" in t-PA comprises at least the arginine residue at position 275. However, various amino acids adjacent to or within several residues of position 275, e.g., up to about 279, are also believed to be a part of the domain recognized by enzymes which convert plasminogen activator to its two-chain form. Thus, replacement of amino acids at positions other than or in addition to 275 within the domain may yield t-PA variants which are resistant to conversion to the two-chain form and/or exhibit more fibrin specificity than wild-type t-PA.

In one particular embodiment, "single-chain plasminogen activator mutant" or "variant" is a plasminogen activator which is resistant to conversion to the two-chain form. It is characterized by single or multiple amino acid substitutions within the region defining the two-chain activation site. As modified, such activation site is not enzymatically recognized, and therefore, not hydrolyzed by enzymes which normally convert plasminogen activator to its two-chain form. In another embodiment, the variants exhibit increased fibrin specificity or both properties.

A variety of methods may be used to induce mutations of underlying DNA so as to prepare the variants hereof. One such method, illustrated herein as a particularly preferred embodiment, comprises first inserting a fragment of the native t-PA gene, containing sequences coding for the region to be mutated, into the replicative form of phage M13mp8 to form M13mp8PA. A synthetic oligonucleotide, complementary to the inserted t-PA sequences but containing one or more nucleotide triplets which code for the amino acid to be substituted, is then annealed to the single stranded form of M13mp8PA to form a double stranded region. This region serves as a primer for DNA polymerase I synthesis of the remaining complementary strand. After replication and identification, the mutant t-PA sequence may be further modified or used to construct a prokaryotic or eukaryotic vector for expressing the mutated t-PA polypeptide.

The variant is assayed for its enzymatic activity by determining the kinetics of conversion of plasminogen to plasmin using the chromogenic plasmin substrate S-2251 in the presence of fibrinogen (or fragments), using the assay described below.

The expression "fibrin specificity" refers to the activity of a variant that exhibits a higher ratio of fibrin-dependent specific activity to fibrinogen-dependent specific activity in a S-2251 assay (in either the one-chain or two-chain form) than wild-type rt-PA, and preferably a ratio of at least 1.5.

As used herein, "transient expression system" denotes a cell culture containing cells transfected with a t-PA variant-encoding vector that expresses the DNA sequence encoding the variant transiently, i.e., in a manner that may not be stable. Such cells are deemed "capable of transient expression."

The t-PA variants herein, in addition to being altered from the native sequence as described herein so as to display certain specific properties, also optionally contain substitutions, deletions, or insertions of residues in other regions of the native sequence of the molecule. These can be considered "bioequivalent molecules".

For example, the variants herein may be suitably devoid of at least a portion of the finger domain, the growth factor domain, and/or the kringle 1 domain, and/or devoid of glycosylation potential at the glycosylation site surrounding amino acid 184 and/or 117, and suitably contain amino acid modifications in the putative lysine binding site of kringle 1 or 2.

Specific examples of such variants include a molecule devoid of amino acids 1 to 44 and a molecule having aspartic acid at position 184. Variants devoid of amino acids 1 to 44 are described more fully in WO 89/00197, supra.

Other examples are where a glycosylation site is inserted in the kringle-1 domain such as the variant T103N. Further examples are where one or more amino acid substitutions are made at positions 94 and 95 or from positions 293–305, and in where the amino acids at positions 466–470 are deleted.

All of the above variants are optionally modified in various other regions of the molecule, if such modifications still satisfy the criteria expressed herein for specific characteristics. Such modifications include, for example:

1. Kringle 1 modifications, for example, deletion of about 92 to 179, and/or

2. Kringle 2 modifications, for example, deletion of about 174–261 or modification in the region of amino acids about 205–215, especially 210–213, and/or 3. Amino acids about 244–255, especially 252 or its site, and/or 4. Amino acids about 233–242, especially 236–238, and/or 5. Known glycosylation sites such as amino acid 184, and/or 6. Glycosylation within the growth factor domain, PCT publication, WO 88/00049 published 12 Jan. 1989, the disclosure of which is incorporated herein by reference. Briefly, the t-PA molecule is N- or O-linked glycosylated within its growth factor domain, preferably at position 67–69, where the tyrosine at position 67 is replaced with an asparagine residue, to alter the half-life of the t-PA molecule.

Many of these modifications may significantly alter clearance rates and fibrin binding relative to native t-PA. The practitioner skilled in the art will be able to determine by the appropriate assay what the optimum properties of each variant are that are desired in any particular instance.

The modification to change or insert the appropriate amino acid(s) in the native molecule to effect the above sequence variations is accomplished by any means known in the art, such as, e.g., site-directed mutagenesis or ligation of the appropriate sequence into the DNA encoding the relevant protein, as described below.

For purposes of shorthand designation of t-PA variants hereof, it is noted that numbers refer to the amino acid residue/position along the 527 amino acid sequence of putative mature t-PA—see EPA 093619, which corresponds to U.S. Pat. No. 4,766,075. See also FIGS. 2a, 2b and 2c herein. Amino acid identification uses the single letter alphabet of amino acids, i.e.:

| Asp | D | Aspartic acid | Ile | I | Isoleucine |
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

The letter appearing before the number is the natural amino acid at that numbered position and the letter appearing after the number is the variant amino acid at that position. In this system, proline substitution at position 276 would be expressed as I276P.

A. General t-PA derivatives hereof are prepared 1) having methionine as its first amino acid (present by virtue of the ATG start signal codon insertion in front of the structural gene) or 2) where the methionine is intra- or extracellularly cleaved, having its normally first amino acid, or 3) together with either its signal polypeptide or conjugated protein other than its conventional signal polypeptide, the signal polypeptide or a conjugate being specifically cleavable in an intra- or extracellular environment, or 4) by direct expression in mature form without the necessity of cleaving away any extraneous, superfluous polypeptide. In all events, the thus produced human mutated t-PA, in its various forms, is recovered and purified to a level suitable for the treatment of various vascular conditions or diseases such as myocardial infarct, strokes, pulmonary embolism, deep vein thrombosis, peripheral arterial occlusion and other thrombotic conditions.

"Expression Vector" includes vectors which are capable of expressing DNA sequences contained therein, where such sequences are operably linked to other sequences capable of effecting their expression and which are replicable in the host organisms, either as episomes or as an integral part of the chromosomal DNA.

"Recombinant host cells" refers to cells which have been transfected with expression vectors constructed using recombinant DNA techniques.

B. Host Cell Cultures and Vectors

The vectors and method disclosed herein are suitable for use in host cells over a wide range of prokaryotic and eukaryotic organisms. For example, *E. coli* K12 strain 294 (ATCC No. 31446) is particularly useful. Other microbial strains which may be used such as *E. coli* B, and *E. coli* X1776 (ATCC No. 31537). These examples are, of course, intended to be illustrative rather than limiting.

In addition to prokaryotes, eukaryotic organisms, such as yeast cultures, may be used. Cultures of cells derived from multicellular organisms are the hosts of choice currently. In principle, any such cell culture is workable; however, interest has been greatest in cells from vertebrates, and propagation of these cells in culture (tissue culture) has become a repeatable procedure—see *Tissue Culture*, Academic Press, Kruse and Patterson, editors (1973). Examples of such useful host cell lines re VERO and HeLa cells, Chinese Hamster Ovary (CHO) cell lines, e.g. DHFR$^+$ CHO-K1 cells (ATCC No. CCL 61), W138, BHK, COS-7, 293 and MDCK cell lines.

Examples which are set forth hereinbelow describe the use of *E. coli* using the trp promoter system and the use of CHO cells using expression vectors which include the SV40 Origin of replication as a promoter. However, it would be well within the skill in the art to use alternative prokaryotic or eukaryotic host cell cultures.

C. Methods Employed

1. Transfection

If cells without formidable cell wall barriers are used as host cells, transfection may be carried out by the calcium phosphate precipitation method as described by Graham, et al., *Virology* 52, 546 (1978). However, nuclear injection or protoplast fusion may also be used.

If prokaryotic cells or cells which contain substantial cell wall constructions are used, the preferred method of transfection is via calcium chloride as described by Cohen, et al., *Proc. Natl. Acad. Sci.* (USA) 69, 2110 (1972).

2. Vector Construction

Construction of suitable vectors containing the desired coding and control sequence employ standard ligation techniques known per se. Isolated plasmids or DNA fragments are cleaved, tailored, and re-ligated in the form desired to form the plasmids required.

3. Site-Specific Mutagenesis

Preparation of t-PA variants in accordance herewith is preferably achieved by site-specific mutagenesis of DNA that encodes an earlier prepared variant or a nonvariant version of the protein. Site-specific mutagenesis allows the production of t-PA variants through the use of specific oligonucleotide sequences that encode the DNA sequence of the desired mutation, as well as a sufficient number of adjacent nucleotides to provide a primer sequence of sufficient size and sequence complexity to form a stable duplex on both sides of the junction being traversed. Typically, a primer of about 20 to 25 nucleotides in length is preferred, with about 5 to 10 residues on both sides of the junction of the sequence being altered. In general, the technique of site-specific mutagenesis is well known in the art as exemplified by publications such as Adelman, et al., *DNA*, 2: 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing, et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira, et al., *Meth. Enzymol.*, 153: 3 (1987)) may be employed to obtain single-stranded DNA.

In general, site-directed mutagenesis in accordance herewith is performed by first obtaining a single-stranded vector that includes within its sequence a DNA sequence that encodes the relevant t-PA. An oligonucleotide primer bearing the desired mutated sequence is prepared, generally synthetically, for example, by the method of Crea, et al., *Proc. Natl. Acad. Sci.* (USA), 75: 5765 (1978). This primer is then annealed with the single-stranded t-PA sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected, via hybridization to a radioactive probe consisting of the $^{32}$P-labeled mutagenesis primer, that include recombinant vectors bearing the mutated sequence arrangement.

After such a clone is selected, the mutated t-PA region may be removed and placed in an appropriate vector for t-PA production, generally an expression vector of the type that typically is employed for transformation of an appropriate eukaryotic host. In the context of the present invention, Chinese hamster ovary (CHO) cells or 293 (human kidney cells described by Graham, et al., *J. Gen. Virol.*, 36: 59 (1977)) are preferred for the preparation of long-term stable t-PA producers. However, the invention is not limited to CHO production, as it is known that numerous other cell types are suitably employed, particularly where one desires only transient production of the enzyme for test purposes. For example, described below is a transient system employing 293 cells that provides a convenient system for production of t-PA variants for analytical purposes.

4. Cleavage/Ligation Technique

Another method for making mutations in the DNA sequence encoding the t-PA involves cleaving the DNA encoding the t-PA at the appropriate position by digestion with restriction enzymes, recovering the properly cleaved DNA, synthesizing an oligonucleotide encoding the desired amino acid and flanking regions such as polylinkers with blunt ends (or, instead of using polylinkers, digesting the synthetic oligonucleotide with the restriction enzymes also used to cleave the t-PA-encoding DNA, thereby creating cohesive termini), and ligating the synthetic DNA into the remainder of the t-PA-encoding structural gene.

5. Host Cell Cultures and Vectors

Although Chinese hamster ovary (CHO) expression ultimately is preferred for t-PA production, the vectors and methods disclosed herein are suitable for use in host cells over a wide range of eukaryotic organisms.

In general, of course, prokaryotes are preferred for the initial cloning of DNA sequences and constructing the vectors useful in the invention. For example, *E. coli* K12 strain 294 (ATCC No. 31,446) and *E. coli* strain W3110 (ATCC No. 27,325) are particularly useful. Other suitable microbial strains include *E. coli* strains such as *E. coli* B, and *E. coli* X1776 (ATCC No. 31,537). These examples are, of course, intended to be illustrative rather than limiting.

Prokaryotes also are useful for expression. The aforementioned strains, as well as bacilli such as *Bacillus subtilis*, and other enterobacteriaceae such as, e.g., *Salmonella typhimurium* or *Serratia marcesans*, and various Pseudomonas species are examples of useful hosts for expression.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar, et al., *Gene*, 2: 95 (1977)). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems (Chang, et al., *Nature*, 375: 615 (1978); Itakura, et al., *Science*, 198: 1056 (1977); Goeddel, et al., *Nature*, 281: 544 (1979)) and a tryptophan (trp) promoter system (Goeddel, et al., *Nucl. Acids Res.*, 8: 4057 (1980); EPO Appl. Publ. No. 36,776), and the alkaline phosphatase systems. While these are the most commonly used, other microbial promoters have been discovered and utilized, and details concerning their nucleotide sequences have been published, enabling a skilled worker to ligate them functionally with plasmid vectors (see, e.g., Siebenlist, et al., *Cell*, 20: 269 (1980)).

In addition to prokaryotes, eukaryotic microbes, such as yeasts, also are suitably used herein. *Saccharomyces cerevisiae*, or common baker's yeast, is the most commonly used among eukaryotic microorganisms, although a number of other strains are commonly available. For example, for expression in Saccharomyces, the plasmid YRp7 (Stinchcomb, et al., *Nature*, 282: 39 (1979); Kingsman, et al., *Gene*, 7: 141 (1979); Tschemper, et al., *Gene*, 10: 157 (1980)) is commonly used. This plasmid already contains the trp1 gene that provides a selection marker for a mutant strain of yeast lacking the ability to grow in tryptophan, for example, ATCC No. 44,076 or PEP4-1 (Jones, *Genetics*, 85: 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., *J. Biol. Chem.*, 255: 2073 (1980)) or other glycolytic enzymes (Hess, et al., *J. Adv. Enzyme Reg.*, 7: 149 (1968); Holland, et al., *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, CHO cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication (Fiers, et al., *Nature*, 273: 113 (1978)). Smaller or larger SV40 fragments are also suitably used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication typically is provided either by construction of the vector to include an exogenous origin, such as may be derived from SV40 or other viral (e.g., Polyoma, Adeno, VSV, BPV) source, or by the host cell chromosomal replication mechanism. If the vector is integrated into the host cell chromosome, the latter is often sufficient.

Satisfactory amounts of human t-PA are produced by cell cultures; however, refinements, using a secondary coding sequence, serve to enhance production levels even further. The secondary coding sequence comprises dihydrofolate reductase (DHFR) that is affected by an externally controlled parameter, such as methotrexate (MTX), thus permitting control of expression by control of the MTX concentration.

In the selection of a preferred host cell for transfection by the vectors of the invention that comprise DNA sequences encoding both variant t-PA and DHFR protein, it is appropriate to consider the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the CHO cell line deficient in DHFR activity, prepared and propagated, as described by Urlaub and Chasin, *Proc. Natl. Acad. Sci.* (USA) 77: 4216 (1980).

On the other hand, if DHFR protein with low binding affinity for MTX is used as the controlling sequence, it is not necessary to use DHFR-deficient cells. Because the mutant DHFR is resistant to MTX, MTX-containing media can be used as a means of selection, provided that the host cells are themselves MTX sensitive. Most eukaryotic cells that are capable of absorbing MTX appear to be sensitive to MTX. One such useful cell line is a CHO line, CHO-K1 (ATCC No. CCL 61).

6. Typical Cloning and Expression Methodology Employable

If mammalian cells are used as host cells, transfection generally is carried out by the calcium phosphate precipitation method as described by Graham and Van der Eb, *Virology*, 52: 546 (1978). However, other methods for introducing DNA into cells such as nuclear injection, electroporation, or protoplast fusion are also suitably used.

If yeast are used as the host, transfection is generally accomplished using polyethylene glycol, as taught by Hinnen, *Proc. Natl. Acad. Sci. U.S.A.*, 75: 1929–1933 (1978).

If prokaryotic cells or cells that contain substantial cell wall constructions are used, the preferred method of transfection is calcium treatment using calcium as described by Cohen, et al., *Proc. Natl. Acad. Sci.* (USA) 69: 2110 (1972), or more recently electroporation.

Construction of suitable vectors containing the desired coding and control sequences employs standard ligation techniques. Isolated plasmids or DNA fragments are cleaved, tailored, and relegated in the form desired to form the plasmids required.

Cleavage is performed by treating with restriction enzyme (or enzymes) in suitable buffer. In general, about 1 µg plasmid or DNA fragments is used with about 1 unit of enzyme in about 20 µl of buffer solution. (Appropriate buffers and substrate amounts for particular restriction enzymes are specified by the manufacturer.) Incubation times of about one hour at 37° C. are workable. After incubation, protein is removed by extraction with phenol and chloroform, and the nucleic acid is recovered from the aqueous fraction by precipitation with ethanol.

If blunt ends are required, the preparation may be treated for 15 minutes at 15° C. with 10 units of the Klenow fragment of DNA Polymerase I (Klenow), phenol-chloroform extracted, and ethanol precipitated.

Size separation of the cleaved fragments is performed using 6 percent polyacrylamide gel described by Goeddel, et al., *Nucleic Acids Res.*, 8: 4057 (1980).

For ligation, approximately equimolar amounts of the desired components, suitably end tailored to provide correct matching, are treated with about 10 units T4 DNA ligase per 0.5 µg DNA. (When cleaved vectors are used as components, it may be useful to prevent relegation of the cleaved vector by pretreatment with bacterial alkaline phosphatase.)

As discussed above, t-PA variants are preferably produced by means of specific mutation. Variants useful in the practice of the present invention are formed most readily through the use of specific oligonucleotide sequences that encode the DNA sequence of the desired mutation, as well as a sufficient number of adjacent nucleotides, to provide a sequence of sufficient size and sequence complexity to form a stable duplex on both sides of the mutation being traversed.

For analysis to confirm correct sequences in plasmids constructed, the ligation mixtures are typically used to transform *E. coli* K12 strain 294 (ATCC 31.446) or other suitable *E. coli* strains, and successful transformants selected by ampicillin or tetracycline resistance where appropriate. Plasmids from the transformants are prepared and analyzed by restriction mapping and/or DNA sequencing by the method of Messing, et al., *Nucleic Acids Res.*, 9: 309 (1981) or by the method of Maxam, et al., *Methods of Enzymology*, 65: 499 (1980).

After introduction of the DNA into the mammalian cell host and selection in medium for stable transformants, amplification of DHFR-protein-coding sequences is effected by growing host cell cultures in the presence of approximately 20,000–500,000 nM concentrations of MTX, a competitive inhibitor of DHFR activity. The effective range of concentration is highly dependent, of course, upon the nature of the DHFR gene and protein and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

In order to simplify the examples certain frequently occurring methods will be referenced by shorthand phrases.

"Plasmids" are designated by a low case p followed by an alphanumeric designation. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 2 units of enzyme in about 20 µl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis, et al., 1982, *Molecular Cloning* pp. 133–134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn, et al., 1981, *Nucleic Acids Res.* 9:6103–6114, and D. Goeddel, et al., 1980, *Nucleic Acids Res.* 8:4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, *J. Mol. Biol.* 98: 503–517, and hybridization as described by T. Maniatis, et al., 1978, *Cell* 15: 687–701.

"Transformation" or "transfection" means introducing DNA into an organism so that the DNA is replicable, either as an extrachromosomal element or chromosomal integrant.

"Ligation" refers to the process of forming phosphodiester bonds between two double stranded nucleic acid fragments (T. Maniatis, et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

"Preparation" of DNA from transformants means isolating plasmid DNA from microbial culture. Unless otherwise provided, the alkaline/SDS method of Maniatis, et al., Id., p. 90, may be used.

"Oligonucleotides" are short length single or double stranded polydeoxynucleotides that are chemically synthesized by known methods and then purified on polyacrylamide gels.

D. Pharmaceutical Compositions

The compounds of the present invention can be formulated according to known methods to prepare pharmaceutically useful compositions, whereby the t-PA product hereof is combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences*, 16th ed., 1980, Mack Publishing Co., edited by Oslo, et al., the disclosure of which is hereby incorporated by reference. Such compositions will typically contain an effective amount of the variant herein, for example, from about 0.5 to about 5 mg/ml, together with a suitable amount of carrier vehicle to prepare pharmaceutically acceptable compositions suitable for effective administration to the host. The t-PA variant herein may be administered parenterally to subjects suffering from cardiovascular diseases or conditions, or by other methods that ensure its delivery to the bloodstream in an effective form.

Compositions particularly well suited for the clinical administration of variant t-PA products employed in the practice of the present invention include, for example, sterile aqueous solutions, or sterile hydratable powders such as lyophilized protein. It is generally desirable to include further in the formulation an appropriate amount of a pharmaceutically acceptable salt, generally in an amount sufficient to render the formulation isotonic. A pH regulator such as arginine base, and phosphoric acid, are also typically included in sufficient quantities to maintain an appropriate pH, generally from 5.5 to 7.5. Moreover, for improvement of shelf-life or stability of aqueous formulations, it may also be desirable to include further agents such as glycerol. In this manner, variant t-PA formulations are rendered appropriate for parenteral administration, and, in particular, intravenous administration.

Dosages and desired drug concentrations of pharmaceutical compositions of the present invention may vary depending on the particular use envisioned. For example, in the treatment of deep vein thrombosis or peripheral vascular disease, "bolus" doses, on the order of about 0.05 to about 0.2 mg/kg, will typically be preferred with subsequent administrations, on the order of about 0.1 to about 0.2 mg/kg, being given to maintain an approximately constant blood level, preferably on the order of about 3 µg/ml.

However, for use in connection with emergency medical care facilities where infusion capability is generally not available and due to the generally critical nature of the underlying disease (e.g., embolism, infarct), it will generally be desirable to provide somewhat larger initial doses, such as an intravenous bolus on the order of about 0.3 mg/kg.

For example, the t-PA variant hereof is suitably administered parenterally to subjects suffering from cardiovascular diseases or conditions. Dosage and dose rate may be parallel to or higher than that currently in use in clinical investigations of other cardiovascular, thrombolytic agents, e.g., about 1–2 mg/kg body weight as an intravenous or intraarterial dose over 1.5 to 12 hours in human patients suffering from myocardial infarction, pulmonary embolism, etc. Higher doses may be tolerated because the variants herein have lower side effects than wild-type t-PA, leading to faster and more complete clot lysis.

As one example of an appropriate dosage form, a vial containing 50 mg t-PA, arginine, phosphoric acid, and polysorbate 80 is reconstituted with 50 ml sterile water for injection and mixed with a suitable volume of 0.9 percent sodium chloride injection.

The t-PA variants herein also are useful to prevent fibrin deposition or adhesion formation or reformation. One embodiment of this use is PCT publication, WO 88/0049, published 12 Jan. 1989, the disclosure of which is incorporated herein by reference. Generally, such treatment involves topical administration of a composition to a site of potential fibrin or adhesion formation wherein the composition comprises a therapeutically effective amount of the t-PA variant in a sparingly soluble form that is continuously released at that site for a period of time of about from three days to two weeks. Typically, the t-PA variant is administered at a dosage sufficient to prevent fibrin deposition or formation of adhesions following surgery, infection, trauma, or inflammation. Typically, this amount is from 0.02 mg/g of gel to 25 mg/g of gel, with preferred amounts from 0.20 mg/g gel to about 2.5 mg/g of gel, most preferably from 0.25 mg/g to about 1.0 mg/g of gel.

The vehicle in which the t-PA is typically formulated for preventing adhesion formation in a semisolid, mucilaginous pharmaceutically inert carrier for positioning the enzyme at the site of potential adhesion formation. Such a carrier includes long-chain hydrocarbons or vegetable oils and waxes composed of mixtures of saturated and unsaturated fatty acid glycerides or mixtures of modified saturated and unsaturated fatty acid glycerides. Examples include semisolid vehicles such as petroleum jelly or semi-synthetic glycerides, polyhydroxy solvents such as glycerol, long-chain hydrocarbons, bioerodable polymers, or liposomes.

The following examples are intended merely to illustrate the best mode now known for practicing the invention, but the invention is not to be considered limited thereto.

All literature and patent application citations herein are expressly incorporated by reference.

E. Examples

Preparation and Utilization of Expression Vector for Recombinant Production of the t-PA Variants Hereof 1. Construction of Plasmid pRK7-t-PA Plasmid pRK7 was used as the vector for generation of the t-PA variants. pRK7 is identical to pRK5 (EP Pub. No. 307,247 published Mar. 15, 1989), except that the order of the endonuclease restriction sites in the polylinker region between ClaI and HindIII is reversed. The t-PA cDNA (Pennica et al., *Nature*, 301: 214 (1983)) was prepared for insertion into the vector by cutting with restriction endonuclease HindIII (which cuts 49 base pairs 5' of the ATG start codon) and restriction endonuclease BalI (which cuts 276 base pairs downstream of the TGA stop codon). This cDNA was ligated into pRK7 previously cut with HindIII and SmaI using standard ligation methodology (Maniatis et al., *Molecular Cloning: A Laboratory Manual,* Cold Spring Harbor Laboratory, New York, 1982). This construct was named pRK7-t-PA.

2. Mutagenesis of Expression Plasmid pRK-t-PA

Site-directed mutagenesis of t-PA cDNA was performed by the method of Taylor et al., *Nucl. Acids. Res.,* 13: 8765 (1985) using a kit purchased from the Amersham Corporation (catalog number RPN 1253). For generation of the desired mutants, oligonucleotides of sequences coding for the desired amino acid substitutions were synthesized and used as primers. These oligonucleotides were annealed to single-stranded pRK7-t-PA that had been prepared by standard procedures (Viera et al., *Meth. Enz.,* 143: 3 (1987)).

A mixture of three deoxyribonucleotides, deoxyriboadenosine (dATP), deoxyriboguanosine (dGTP), and deoxyribothymidine (dTTP), was combined with a modified thiodeoxyribocytosine called dCTP(aS) provided in the kit by the manufacturer of the kit, and added to the single-stranded pRK7-t-PA to which was annealed the oligonucleotide.

Upon addition of DNA polymerase to this mixture, a strand of DNA identical to pRK7-t-PA except for the mutated bases was generated. In addition, this new strand of DNA contained dCTP(aS) instead of dCTP, which served to protect it from restriction endonuclease digestion. After the template strand of the double-stranded heteroduplex was nicked with an appropriate restriction enzyme, the template strand was digested with ExoIII nuclease past the region that contained the mutagenic oligomer. The reaction was then stopped to leave a molecule that was only partly single-stranded. A complete double-stranded DNA homoduplex molecule was then formed by DNA polymerase in the presence of all four deoxyribonucleotide triphosphates, ATP, and DNA ligase.

Figure 1:
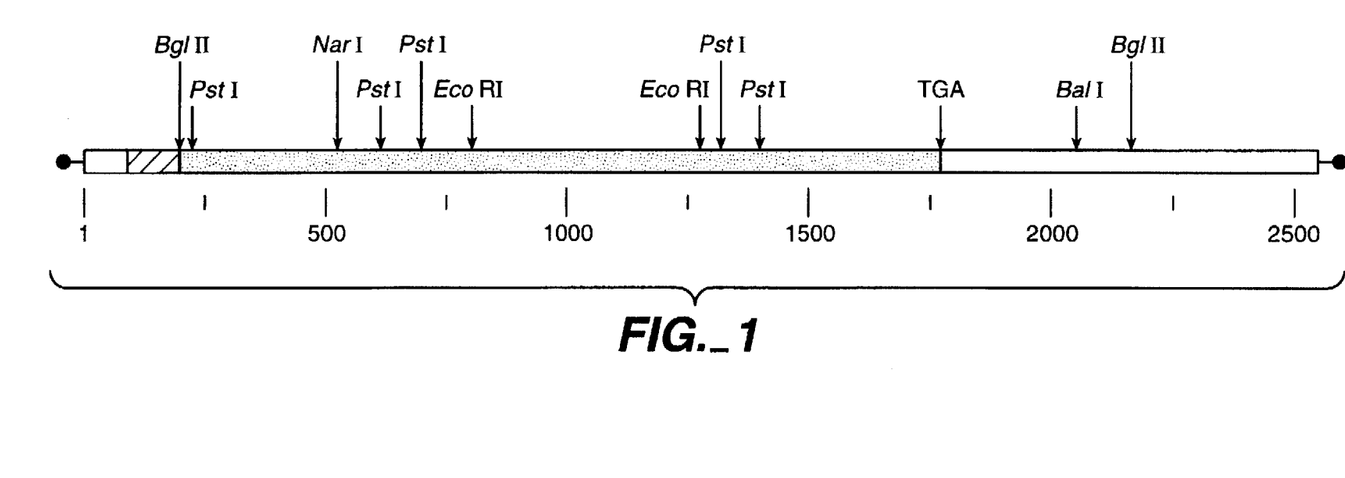
FIG. 1 is a restriction map of the DNA of human t-PA and includes 5' and 3'-untranslated regions as well as sequences encoding pre-t-PA. The speckled area represents the structure gene for t-PA.
Figure 3:
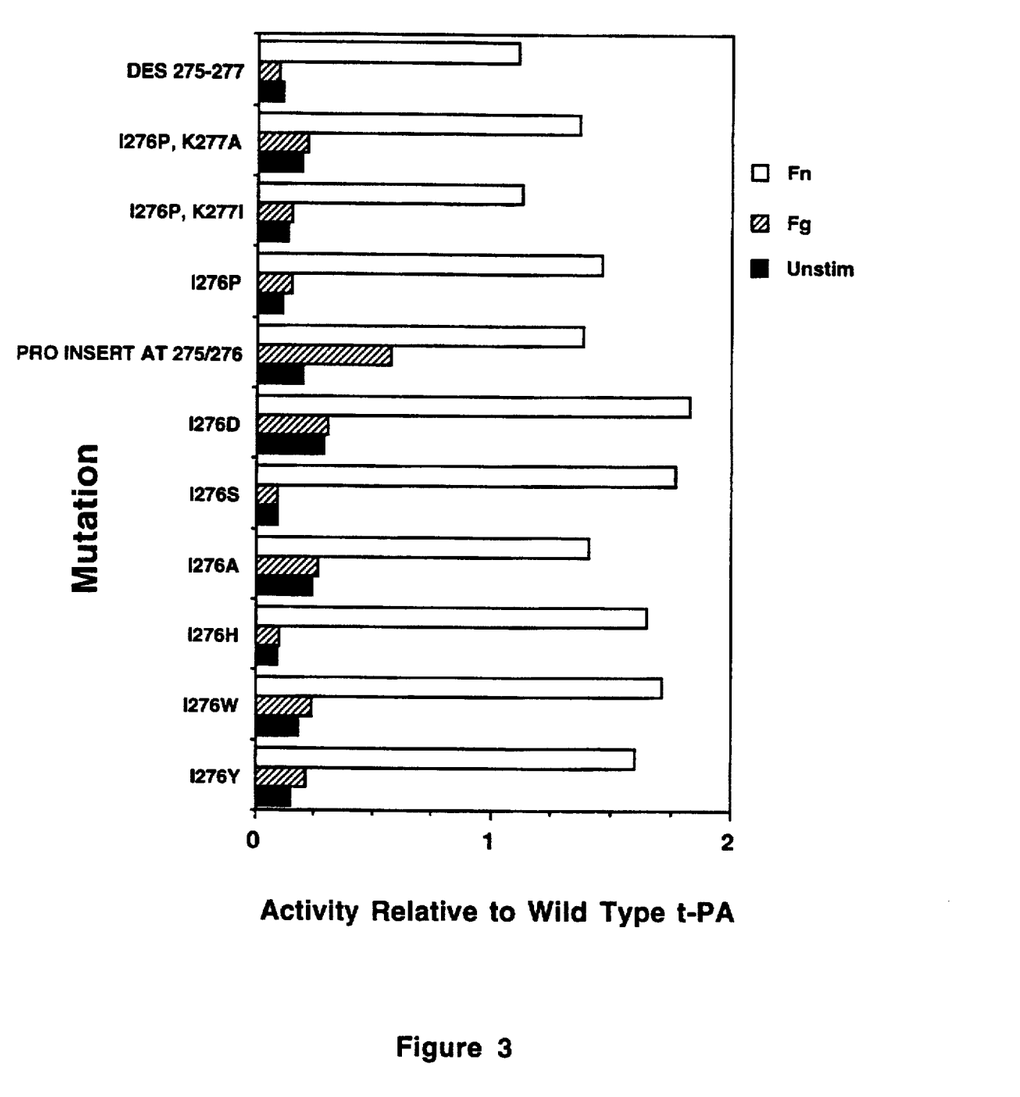
FIG. 3 depicts the activity of the t-PA variants at the 276 position relative to wild-type t-PA (activity=1.0) in the S-2251 assay. In this figure, the letter appearing before the number is the natural amino acid at that numbered position and the letter appearing after the number is the variant amino acid at that position. "Fn" indicates the addition of fibrinogen and thrombin such that the assay is performed in the presence of fibrin. "Fg" indicates addition of fibrinogen alone. "Unstim" indicates only the t-PA variant and plasminogen are present in addition to the S-2251 substrate.

The following oligonucleotides were prepared to use as primers to generate pRK7-t-PA molecules:

| Variant* | Oligo Number | Sequence |
| --- | --- | --- |
| Des275-277 | 437 | GGCGAAGAGCCCTCCAAACTGAGGCTG |
| Pro Insert at 275/276 | 466 | GAGCCCTCCTTTGATGGGGCGAAACTG-AGGCTG |
| I276P | 439 | GAGCCCTCCTTTGGGGCGAAACTGAGG |
| I276P, K277I | 467 | GAAGAGCCCTCCAATGGGGCGAAACTGAGG |
| I276P, K277A | 468 | GAAGAGCCCTCCGGCGGGGCGAAACTGAGG |
| I276D | 469 | CCCTCCTTTATCGCGAAACTGAGG |
| I276H | 470 | CCCTCCTTTGTGGCGAAACTGAGG |
| I276Y | 471 | CCCTCCTTTATAGCGAAACTGAGG |
| I276A | 472 | CCCTCCTTTGGCGCGAAACTGAGG |
| I276W | 473 | CCCTCCTTTCCAGCGAAACTGAGG |
| I276S | 474 | CCCTCCTTTAGAGCGAAACTGAGG |
| F274L, R275H, I276S, K277T | 449 | GGCGAAGAGCCCTCCGGTAGAGTGTAAC-TGAGGCTGGCTGTA |

*Notations: Letter to left of amino acid position numeral is natural amino acid at that position and letter to right is the variant amino acid. See FIG 3.

3. Bacterial Transformation and DNA Preparation

The variant t-PA constructs generated using the protocol above were transformed into *E. colihost* strain MM294tonA using the standard CaCl$_2$ procedure (Maniatis et al., supra) for preparation and transformation of competent cells. MM294tonA (which is resistant to T1 phage) was prepared by the insertion and subsequent imprecise excision of a Tn10 transposon into the tonA gene. This gene was then inserted, using transposon insertion mutagenesis (Kleckner et al., *J. Mol. Biol.,* 116: 125–159 (1977)), into *E. coli* host MM294 (ATCC 31,446).

Individual colonies of bacterial transofrmants were selected and grown to saturation in 35 ml LB broth containing 150 µg/ml carbenicillin. DNA was extracted and purified using a kit purchased from Qiagen Inc. (catalog number 41021). The plasmids were analyzed by sequencing and by restriction endonuclease digestion and agarose gel electrophoresis.

4. Transfection of Human Embryonic Kidney 293 Cells (Small-Scale)

293 cells were grown to 70% confluence in 6-well plates. 2.5 µg of t-PA plasmid DNA mutant was dissolved in 150 ml of 1 mM Tris-HCl, 0.1 mM EDTA, 0.227 M CaCl$_2$. Added to this (dropwise while vortexing) was 150 µl of 50 mM HEPES buffer (pH 7.35), 280 mM NaCl, 1.5 mM NaPO$_4$, and the precipitate was allowed to form for ten min. at 25° C. The suspended precipitate was then added to the cells in the individual wells in a 6-well plate and allowed to settle for four hours in the incubator. The medium was then aspirated off and 1 ml of 20% glycerol in PBS was added for 30 sec. The cells were washed twice, first with 3 ml, then with 1 ml, of serum-free medium. Then 3 ml of fresh medium was added and the cells were incubated for five days. The medium was then collected and assayed.

When single-chain t-PA was required, the procedure was as described above except that plasminogen-depleted serum was used during the growth phase of the cells.

Biological Assay

A. t-PA Quantitation

The amount of t-PA present in the cell culture supernatants was determined by the ELISA procedure using polyclonal antibodies prepared against wild-type t-PA.

B. S-2251 Assay (Plasminogen Activator Assay)

This assay is an indirect assay for t-PA activity. In this assay, plasminogen is converted to plasmin by the action of t-PA, and plasmin cleaves the S-2251 substrate to release the paranitroanilide chromophore. Production of this chromophore is measured over time. The protocols for the fibrin-stimulated, fibrinogen-stimulated, and unstimulated assay have been detailed previously (Bennett et al., JBC 266, pp 5191–5201, (1991)). For this study, all samples were incubated with sepharose-plasmin prior to assay. Samples susceptible to cleavage by plasmin were converted to the two-chain form during this step.

The variants prepared using the oligonucleotides set forth above (Oligo numbers 437, 439 and 466 to 474) when tested for activity according to the S-2251 assay gave the results set forth in FIG. 3.

From this data, it can be seen that in the presence of fibrin all of the variants exhibited plasminogen activator activity which was equal to or greater than that of wild type t-PA. In contrast, these variants had lower than wild-type activity in the presence of fibrinogen, or in the absence of a stimulator. These results indicate that the variants are more fibrin specific than wild-type t-PA.

The fold increase in fibrin specificity for these variants over that of wild-type t-PA was determined by taking the ratio of the relative activities of the variants in the presence of fibrin to that in the presence of fibrinogen. The results are shown in Table I below. In our hands, the plasminogen activator activity of wild-type t-PA in the S-2251 assay is approximately six-fold greater when fibrin is used compared to fibrinogen (Bennett et al., JBC 266, pp 5191–5201, (1991)). The values for the variants are in excess to that difference.

TABLE I

| Mutant | Activity Ratio (Fibrin/Fibrinogen) |
| --- | --- |
| Des 275–277 | 12.3 |
| I276P, K277A | 6.5 |
| I276P, K277I | 7.5 |
| I276P | 9.7 |
| Pro insert at 275/276 | 2.4 |
| I276D | 6.0 |
| I276S | 19.7 |
| I276A | 5.4 |
| I276H | 16.5 |
| I276W | 7.1 |
| I276Y | 7.6 |

Having described the preferred embodiment of the present invention, it will appear to those ordinarily skilled in the art that various modifications may be made to the disclosed embodiment, and that such modifications are intended to be within the scope of the present invention.

What is claimed is:

1. A human tissue plasminogen activator (t-PA) having an amino acid other than isoleucine substituted at position 276 of the amino acid sequence of wild-type t-PA.

2. A t-PA according to claim 1 wherein said amino acid is proline.

3. A t-PA according to claim 1 wherein said amino acid is aspartic acid.

4. A t-PA according to claim 1 wherein said amino acid is serine.

5. A t-PA according to claim 1 wherein said amino acid is alanine.

6. A t-PA according to claim 1 wherein said amino acid is histidine.

7. A t-PA according to claim 1 wherein said amino acid is tryptophan.

8. A t-PA according to claim 1 wherein said amino acid is tyrosine.

9. A DNA sequence encoding a t-PA according to claim 1.

10. An expression vector capable of expressing the DNA according to claim 9.

11. A cell culture transfected with the vector according to claim 10.

12. A method for expressing a tissue plasminogen activator t-PA which comprises the step of using the DNA according to claim 9 as a template for expression to produce the encoded t-PA as an expression product.

13. A composition for treating cardiovascular disease comprising a therapeutically effective amount of a t-PA according to claim 1 in admixture with a pharmaceutically acceptable carrier.

14. A method of treating cardiovascular disease in a mammal which comprises administering an effective amount of a composition according to claim 13.

15. I276P human tissue plasminogen activator.

16. Des 275–277 human tissue plaminogen activator.

17. A human tissue plasminogen activator (t-PA) with a proline inserted between positions 275/276.

18. A human tissue plasminogen activator (t-PA) selected from the group consisting of I276P, K277I t-PA and I276P, K277A t-PA.

* * * * *